United States Patent
Dzwiniel et al.

(10) Patent No.: US 10,099,994 B2
(45) Date of Patent: Oct. 16, 2018

(54) PROCESS FOR THE PRODUCTION OF HIGH VOLTAGE ELECTROLYTE SOLVENTS FOR LI-ION BATTERIES

(71) Applicants: Trevor L. Dzwiniel, Carol Stream, IL (US); Krzysztof Pupek, Plainfield, IL (US); Gregory K. Krumdick, Homer Glen, IL (US)

(72) Inventors: Trevor L. Dzwiniel, Carol Stream, IL (US); Krzysztof Pupek, Plainfield, IL (US); Gregory K. Krumdick, Homer Glen, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

(21) Appl. No.: 15/262,603

(22) Filed: Sep. 12, 2016

(65) Prior Publication Data
US 2018/0072650 A1    Mar. 15, 2018

(51) Int. Cl.
*C07C 68/06* (2006.01)
*H01M 10/0525* (2010.01)
*H01M 10/0569* (2010.01)

(52) U.S. Cl.
CPC .......... *C07C 68/06* (2013.01); *H01M 10/0525* (2013.01); *H01M 10/0569* (2013.01)

(58) Field of Classification Search
None
See application file for complete search history.

(56) References Cited

U.S. PATENT DOCUMENTS

| 5,659,062 A | 8/1997 | Yokoyama et al. |
| 2012/0141870 A1 | 6/2012 | Chen et al. |
| 2015/0235772 A1 | 8/2015 | Sakata et al. |

OTHER PUBLICATIONS

Ishimoto et al., Development of a Scalable Synthesis of a Vascular Endothelial Growth Factor Receptor-2-Kinase Inhibitor: Efficient Construction of a 6-Etherified [1,2,4]Triazolo[1-5a]pyridine-2-amine Core. Organic Process Research & Development, 2014, 18, 122-134.*
Lopez-Tapia et al., Novel Series of Dihydropyridinone P2X7 Receptor Antagonists. Journal of Medicinal Chemistry, 2015, 58, 8413-8426 (including supporting information).*
Dunn et al., The Safe Use of Sodium Hydride on Scale: The Process Development of a Chloropyrimidine Displacement. Organic Process & Development, 2011, 15, 1442-1446.*

* cited by examiner

*Primary Examiner* — Po-Chih Chen
(74) *Attorney, Agent, or Firm* — Cherskov Flaynik & Gurda, LLC

(57) ABSTRACT

A method for producing halogenated carbonates is provided, the method having the steps of reacting a halogenated hydroxyl moiety with an alkyl formate in the presence of a liquid solvent and a solid base. An exemplary halogenated carbonate so produced is trifluoroethyl methyl carbonate.

11 Claims, 1 Drawing Sheet

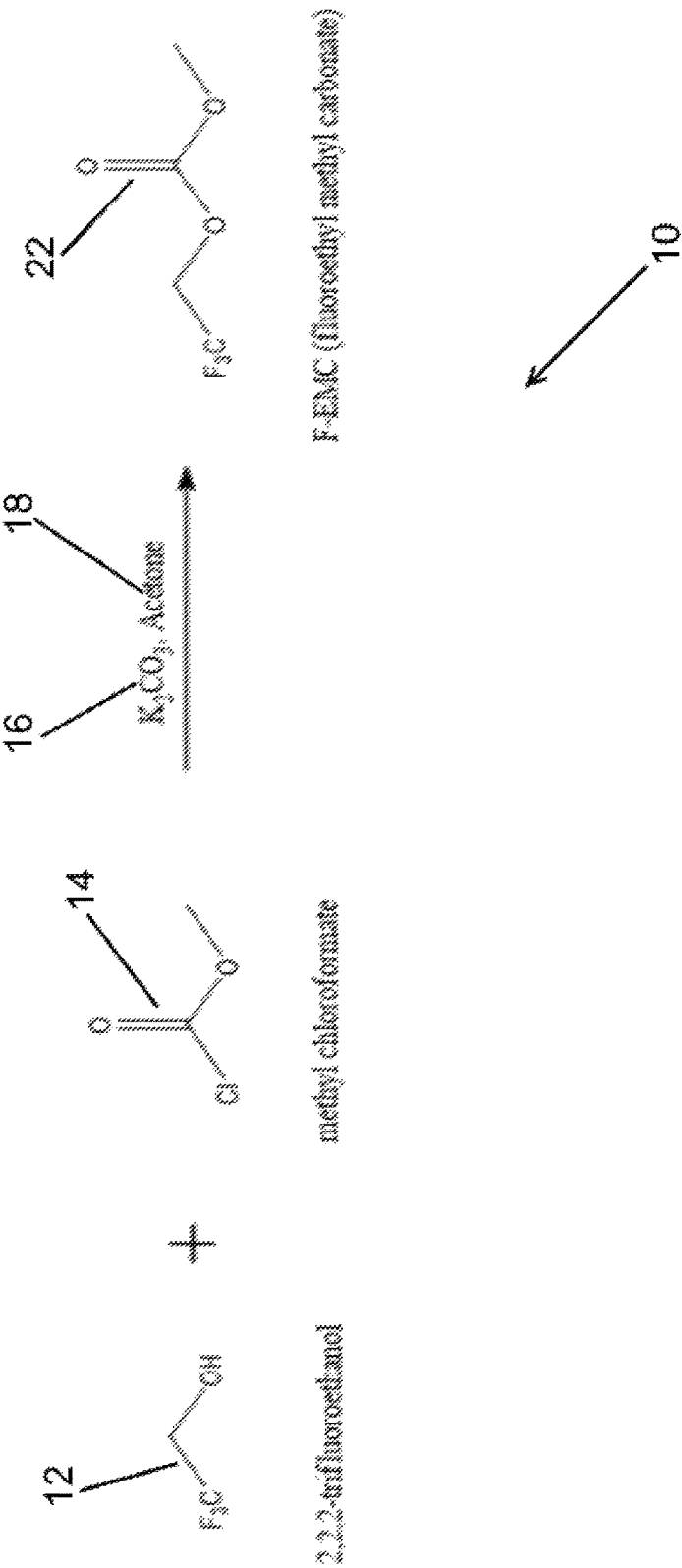

PROCESS FOR THE PRODUCTION OF HIGH VOLTAGE ELECTROLYTE SOLVENTS FOR LI-ION BATTERIES

CONTRACTUAL ORIGIN OF THE INVENTION

The U.S. Government has rights in this invention pursuant to Contract No. DE-AC02-06CH11357 between the U.S. Department of Energy and UChicago Argonne, LLC, representing Argonne National Laboratory.

BACKGROUND OF THE INVENTION

1. Field of the Invention

This invention relates to electrolyte solvents and more specifically, this invention relates to a method for producing high voltage electrolyte solvents for batteries.

2. Background of the Invention

State of the art methods for making electrolyte solvents typically require severe reactants and reaction conditions. Halogenated solvents (e.g., carbon tetrachloride and dichloromethane) are often required. Organic bases, including amines are often utilized. For example, in protocols for producing fluorinated carbonate solvents, dichloromethane and trialkylamine are employed as solvent and base respectively in the reaction of the fluorine containing substrate with methyl chloroformate. These are highly inefficient procedures (30-40 percent yields) that require additional aqueous treatments to remove byproducts and residual reagents. Other protocols using pyridine instead of trialkylamine have similarly low yields (46 percent). These yields result in the generation of significant amounts of waste.

Furthermore, purification of fluorinated carbonate solvents is a difficult fractional distillation, reported to require a spinning column. Azeotropic mixtures are often formed between the formed solvent product and the aforementioned reaction solvents. (When azeotropic mixtures are boiled, the condensate has the same proportions of constituents as the pot mixture. As such, constituents cannot be separated via distillation.)

Some efforts to produce the targeted compounds incorporate higher boiling point solvents, compared to the boiling points of the intended products. Theoretically, the lower point products should boil off first during distillation. As such, relatively lower boiling point reagents are typically avoided.

Also state of the art methods for producing the electrolyte solvents often require strictly anhydrous reaction conditions. As such, nitrogen-filled gloveboxes are required. Overall, this results in a process that is too costly and too cumbersome to be commercially viable.

In light of the foregoing drawbacks, state of the art methods for producing new electrolyte solvents often need to be conducted in controlled atmospheres (e.g., glove boxes). These processes typically require 8-20 hours for completion.

Another drawback to state of the art protocols is the extensive use of halogenated reactants, such as halogenated solvents including dichloromethane. Such chlorinated compounds wreak havoc in battery chemistries if left as residual impurities. In light of the foregoing, extensive filtration and purification protocols are required to remove halogenated moieties.

A need exists in the art for a method for economically producing electrolyte solvent. The method should use relatively mild reaction conditions, eliminate the need for halogenated solvents, and require moderate temperatures of between −10 and 20° C. The method should also not require special reaction atmospheres. Also, the method should not generate significant waste streams and should yield pure product with a limited number of purification steps. Lastly, the method should require no more than four hours, and preferably between about 1 and 4 hours. All of the above conditions need to be met to make the process commercially viable.

SUMMARY OF INVENTION

An object of the invention is to provide a method for producing electrolyte solvent that overcomes many of the drawbacks of the prior art.

Another object of the invention is to provide a method for producing halogenated carbonate solvent, for example chlorinated or fluorinated carbonate solvents, and typically fluorinated solvents. A feature of the invented method is its utilization of a common solvent and a mild base for reactants. An advantage of the invented method is that it takes between about 1 and about 4 hours to complete. Another advantage is that it occurs at temperatures of between about −10° C. and about 20° C.

Yet another object of the present invention is to provide a method for producing trifluoroethyl methyl carbonate. A feature of the method is the use of acetone and potassium carbonate as the solvent and base, respectively. An advantage of the invented method is that ambient atmosphere and pressures can be utilized such that no anhydrous or high pressure environs are required, nor are glove boxes required.

Briefly, the invention provides a method for producing halogenated carbonates, the method comprising reacting a halogenated hydroxyl moiety with an alkyl chloroformate in the presence of a liquid solvent and a solid base. The halogenated moiety comprises fluorine and alcohol. The liquid solvent is a nonhalogenated compound selected from the group consisting of acetone, diethyl ketone, ethyl methyl ketone, acetophenone, cyclohexyl methyl ketone and combinations thereof. The solid base is a carbonate selected from the group consisting of alkali carbonate, alkaline earth carbonate, alkali phosphate, alkaline earth phosphate, and combinations thereof.

BRIEF DESCRIPTION OF DRAWING

The invention together with the above and other objects and advantages will be best understood from the following detailed description of the preferred embodiment of the invention shown in the accompanying drawings, wherein:

FIG. 1 is a chemical reaction sequence for a method for producing halogenated carbonates, in accordance with features of the present invention.

DETAILED DESCRIPTION OF THE INVENTION

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant FIGURE.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Halogenated carbonates are a family of solvents that show promise in high voltage battery prototypes.

The invention provides a process for generating halogenated carbonates using common non-chlorinated solvents and inorganic bases. The instant protocol replaces the anhydrous, highly basic prior art protocols with a low solvent boiling, solid base reactant system to yield high purity product with simple liquids/solids filtration.

A salient feature of the invention is that its use of inorganic (and often solid phase) bases facilitates their separation from product liquor, more so than the prior art uses of organic bases such as amines. For example, when solid phase bases are used, the large majority of the solid phase, e.g., more than 50 percent, and often more than 95 percent, so typically between 50 and 95 percent) remains a solid during the reaction. For example, potassium carbonate has a solubility of 1.3 parts per million in acetone, such that 99 percent of the base remains a solid. These solids are easily removed with a single filtration step. Therefore, the invented protocol can utilize all solid phase bases, or at least a portion of the bases as solid, with the remaining portion being liquid phase. In summary of this point, a salient point of the invention is the use of acetone with a solid phase base having very limited solubility (between 1 and 10 ppm) therein.

An embodiment of the invention provides a process for producing trifluoroethyl methyl carbonate for use as a high voltage electrolyte solvent for lithium ion batteries. The process utilizes common ketones (e.g. acetone) for solvents and heterogeneous, non-amine bases such as carbonates (alkali and alkaline earth metals such as potassium carbonate). This results in an easier to handle, less hazardous process which does not require aqueous workup and which generates less waste. A single filtration and distillation results in yields higher than 60 percent, and purities greater than 99 percent, specifically 99.5 percent.

A salient feature of the invented method is the elimination of any aqueous wash steps. As such, the invented process requires no aqueous wash step.

In an embodiment of the invention, methyl chloroformate is added slowly to a cold suspension of potassium carbonate, trifluoroethanol and low boiling solvent such as acetone. After the reaction is complete, the solids are filtered away. The acetone is removed by distillation and the product is fractionally distilled. Distillation is simplified though the use of the aforementioned non-azeotropic solvent (acetone) and readily-removed solid phase base.

FIG. 1 depicts a chemical equation for the invented reaction sequence, the sequence designated therein as numeral 10. A triple halogenated ethanol 12 is combined with methyl chloroformate 14 in the presence of potassium carbonate 16, and acetone 18. Fluorinated product 22 produced is 2,2,2-trifluoroethyl methyl carbonate (designated throughout this specification as F-EMC).

F-EMC is produced via the invented method using ambient temperature and a solid non-amine base. Byproducts are removed via simple filtration. No aqueous wash is required. The invented process embodies a heterogeneous reaction in that a liquid solvent is combined with a solid base. Suitable liquid solvent can be ketone selected from the group consisting of acetone, diethyl ketone, ethyl methyl ketone, acetophenone, cyclohexyl methyl ketone and combinations thereof.

Use of acetone as the liquid solvent produced unexpected results. Dichloromethane has a boiling point (40° C.) that is further from the boiling point of the fluorinated product (104-106° C.) than acetone's boiling point (56° C.). One of ordinary skill in the art would have predicted that separation of dichloromethane from the fluorinated product would have been easier than separating acetone from the product, Surprisingly, the inventor's found that acetone was more readily removable from a mixture with the fluorinated product than dichloromethane, the standard solvent used in the prior art.

The inventors found that inasmuch as solid bases do not dissolve as readily as organic, liquid bases, their removal from the product mixture is easier to accomplish, therefore leading to a higher purity product. This feature reduces processing time and reduces loss and waste. Suitable solid bases can be a carbonate or phosphate selected from the group consisting of alkali carbonate, alkaline earth carbonate, alkali phosphate, alkaline earth phosphate, and combinations thereof.

The invented process replaces homogeneous reaction protocols. Specifically, the invented process eliminates the need for anhydrous solvents and amine bases (such as pyridine or triethylamine).

The invented process uses a common solvent and a mild base for reactants, thus requiring only mild reaction conditions. Specifically, the invented process does not need to take place at extreme temperatures. The invented process can be run at temperatures as high as right below the boiling point of the solvent (e.g. 56° C. when acetone is used). However, the invented process produces halogenated carbonate solvents at temperatures between about −10° C. and about 20° C., preferably between about 5° C. and about 15° C. to provide high yields of product without the need for elaborate separation steps such as spinning band columns.

Example

A glass reactor (20 L, jacketed, Chemglass) equipped with drain valve, internal temperature probe, addition port, condenser, and gas inlet/outlet adapters was flushed with nitrogen. The jacket of the reactor was connected to a heating/chilling circulator. The gas outlet port was connected to a silicon oil bubbler.

The reactor was charged with acetone and potassium carbonate was added with stirring. The mixture was cooled to 10° C. and 2,2,2-trifluoroethanol was added, generating a 3° C. temperature rise. The mixture was cooled to 10° C. again, and methyl chloroformate was added by peristaltic pump at 5-6 ml/min. The addition was approximately 90 minutes. The reaction was warmed to ambient temperature and followed by GC analysis. When no further reaction was observed, the mixture was filtered and washed with acetone (1 L). The filtrate was held overnight.

The filtrate was rotovaped at 325 mbar/35° C. bath temperature until distillation slowed nearly to a halt. The liquid was transferred to a 5 L jacketed reactor and fractionally distilled through a 10 plate Oldershaw column at 270 down to 105 Torr, the pure fractions distilling at 68° C., 105 torr. Fractions were analyzed by GC/MS prior to combining.

Three identical runs were made. Combined off-fractions were re-distilled, and all samples analyzed before finally combining in lot.

Overall yield was 61%. Additional impure fractions (ca. 20% additional yield) were retained.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those having skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods. As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A method for producing halogenated carbonates, the method comprising:
reacting a halogenated hydroxyl moiety with methyl chloroformate in the presence of a nonhalogenated compound selected from the group consisting of acetone, diethyl ketone, ethyl methyl ketone, acetophenone, cyclohexyl methyl ketone and combinations thereof, and a solid base, wherein the solid base is an inorganic compound selected from the group consisting of alkali carbonate, alkaline earth carbonate, alkali phosphate, alkaline earth phosphate, and combinations thereof.

2. The method as recited in claim 1 wherein the halogenated hydroxyl moiety is a fluorinated alcohol.

3. The method as recited in claim 1 wherein the reaction occurs in ambient atmosphere.

4. The method as recited in claim 1 wherein the halogenated carbonates are produced in about 1 to about 4 hours.

5. The method as recited in claim 1 wherein the halogenated carbonates are produced at temperatures between about −10° C. and about 20° C.

6. The method as recited in claim 1 wherein the halogenated carbonate is trifluoroethyl methyl carbonate.

7. The method as recited in claim 1 wherein the nonhalogenated compound is acetone and the base is potassium carbonate.

8. The method as recited in claim 1 wherein the halogenated hydroxyl moiety is trifluoroethanol.

9. The method as recited in claim 1 wherein the halogenated carbonates are produced having greater than 99.5 percent purity after a single filtration step.

10. The method as recited in claim 1 wherein no aqueous wash is required.

11. The method as recited in claim 1 wherein between 50 and 95 percent of the solid base remains a solid during the reaction.

* * * * *